United States Patent [19]

Brunck et al.

[11] Patent Number: 4,999,421

[45] Date of Patent: Mar. 12, 1991

[54] HTLV-I ANTI-SENSE RNA AND ENCODED PROTEINS

[75] Inventors: Terence K. Brunck, Alameda; David J. Larocca, San Leandro; John J. Monahan, Orinda, all of Calif.

[73] Assignee: Triton Biosciences Inc., Alameda, Calif.

[21] Appl. No.: 211,749

[22] Filed: Jun. 27, 1988

[51] Int. Cl.$^5$ ............................................... C07K 13/00
[52] U.S. Cl. ........................................ 530/350; 435/6; 514/25; 530/806
[58] Field of Search ............... 530/324, 350, 387, 806; 435/6; 424/86; 514/25

[56] References Cited

PUBLICATIONS

Chem. Abs., vol. 108, 1988, 162396j, Miller et al.
Chem. Abs., vol. 109, 1988, 184446y, Goodchild et al.
Chem. Abs. 103, 32864w (1985) Okamoto et al., [Virology, 1985, 143(2), 636-9].
Proc. Natl. Acad. Sci. U.S.A., vol. 81, pp. 6202-6206 (10/1984), Kiyokawa et al.
Chem. Abs. 111(13), 110249f (1988), Gilboa [Adv. Exp. Med. Biol. 241 (Mol. Biol. Hemopoiesis) 29-33 (1988)].
Virology, 136, 338-347 (1984), Hattori et al.
J. Goodchild et al. "Inhibition of Human Immunodeficiency Virus Replication by Antisense Oligonucleotides", Proc. Natl. Acad. Sci. U.S.A. 85: 5507-5511 (Aug. 88).
R. Miller, "Human Immunodeficiency Virus May Encode a Novel Protein on the Genomic DNA Plus Strand", Science 239: 1420-1422 (Mar. 18, 1988).

*Primary Examiner*—Johnnie R. Brown
*Assistant Examiner*—T. D. Wessendorf
*Attorney, Agent, or Firm*—Shelley Precivale; Al Jecminek; Karen Babyak Dow

[57] ABSTRACT

The mRNA coded by the "anti-sense" strand of the complementary DNA produced by HTLV-I infection contains significant open reading frames. Cells infected by HTLV-I virus produce mRNA that is anti-sense to the viral RNA genome. Infected cells may produce proteins from the newly discovered mRNA. The production of the anti-sense in mRNA initiates from a newly discovered transcriptional promoter located within 1.8 kb from the 3' terminus of the viral genome. The mRNA, protein, and antibodies directed thereto can be used in the prevention, diagnosis, and treatment of HTLV-I infections.

1 Claim, 6 Drawing Sheets

HTLV-I ANTI-SENSE RNA AND ENCODED PROTEINS

BACKGROUND OF THE INVENTION

Retroviruses are causative agents for many human and animal diseases. They differ from other viruses in that the genetic information of the retrovirus is carried in the viral particle in the form of single-stranded RNA (sense viral RNA) and in the host cells as double-stranded DNA called the provirus. In the case of human and animal lymphotrophic retroviruses, the genome consists of about 9000 bases, including sequences called long terminal repeats (LTR's) of about 700–800 bases at each end of the provirus. Previous studies of human lymphotrophic retroviruses (HTLV-I HTLV-II, and HIV) have identified a number of proteins that are coded directly in the RNA of the various retroviruses.

Figure 1:
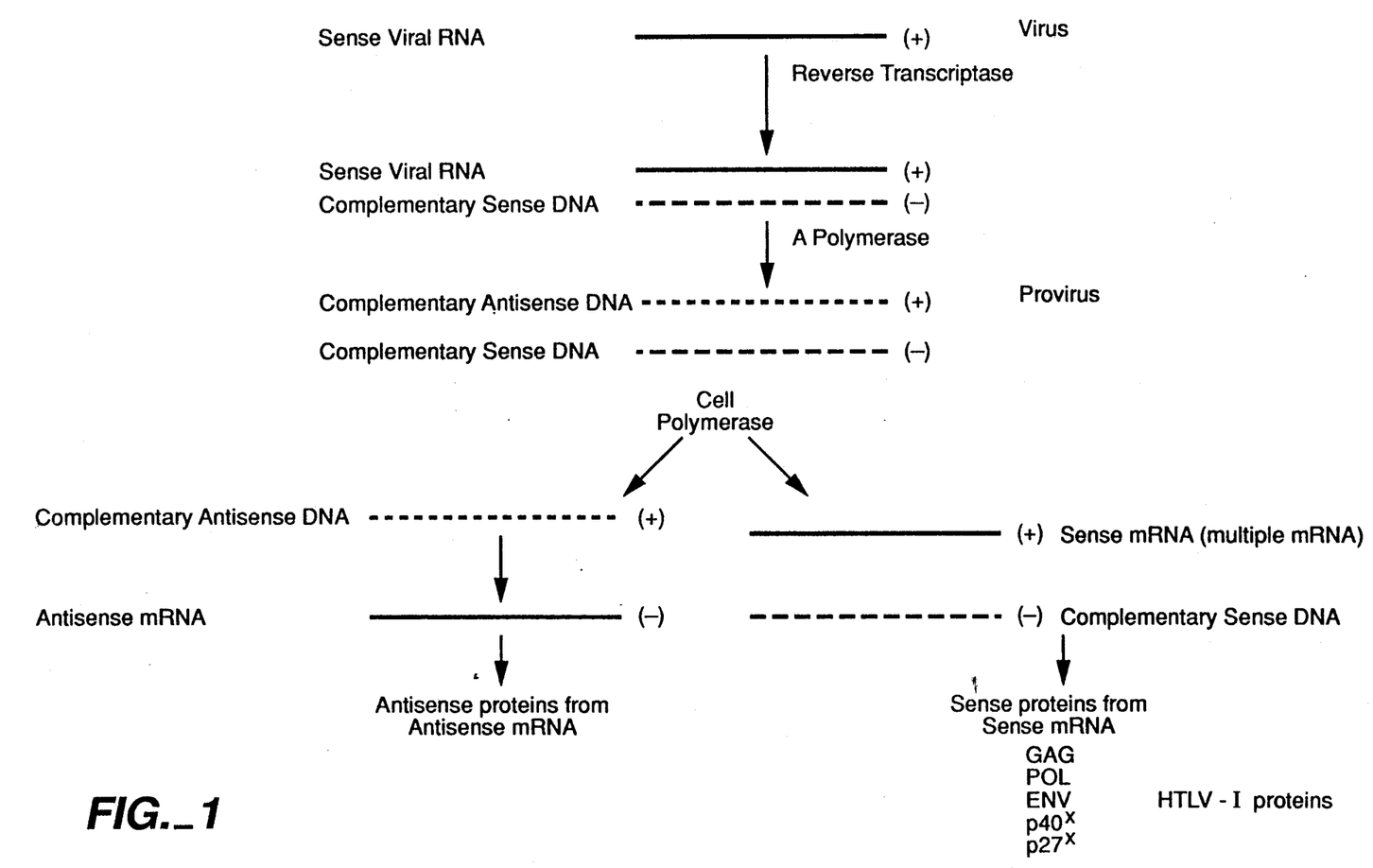
FIG. 1 is a schematic showing the processes by which sense and anti-sense proteins are made from the HTLV-I retroviral genome.

Retroviral viral particles consist of, in part, envelope (env), group-associated antigens (gag), and reverse transcriptase (pol) proteins together with the RNA genome. Upon infection of a host cell, the reverse transcriptase enzyme uses the sense viral RNA as a template to construct a cDNA molecule (complementary sense DNA; see FIG. 1) complementary to the viral RNA from nucleic acids present in the host cell. The complementary sense DNA molecule is then used as a template by a polymerase to produce a double-stranded DNA, one strand of which corresponds to the original sense viral RNA. This double-stranded DNA copy of the viral RNA (the provirus) then integrates into the host genome and begins to produce viral RNA, mRNA, and proteins. Naturally occurring retroviruses contain all the information required to generate many new retroviral particles from one host cell infection event.

Prior to the present invention, those skilled in the art have only studied the proteins and RNA coded directly by the "sense strand" of the HTLV-I retroviral genome (sense viral RNA and sense mRNA). By identifying open forward reading frames in the sense RNA, many lymphotrophic retroviral proteins have been characterized. We have used this approach to identify proteins coded for on the "anti-sense" mRNA. Moreover, we have detected this anti-sense mRNA and, therefore, proteins encoded by this anti-sense mRNA may be present in HTLV-I infected cells. Further, patients infected with HTLV-I may make antibodies against these anti-sense strand encoded proteins.

SUMMARY OF THE INVENTION

In the present invention, we have discovered that the mRNA coded by the "anti-sense" strand of the complementary DNA produced by HTLV-I infection contains significant open reading frames, that cells infected by HTLV-I virus produce mRNA that is "anti-sense" to the viral RNA genome and that infected cells may produce novel proteins from the newly discovered mRNA. Further, we have discovered that the production of the anti-sense mRNA complementary to the viral RNA genome initiates from a newly discovered transcriptional promoter located within 1.8kb from the 3' terminus of the proviral genome.

The novel mRNA, proteins, protein fragments, and antibodies directed thereto have utility in that they may be used in a diagnostic assay. The presence of antibodies to the novel proteins and/or antigenic sites represented by protein fragments may be used to determine if a patient has been infected with the HTLV-I virus, since ATL patients often generate antibodies to retroviral proteins and/or protein fragments. Assays based on detection of antibodies to the novel proteins and/or the novel proteins themselves may also have prognostic value. In addition, nucleic acid probe technology such as that used in nucleic acid amplification techniques, e.g. polymerase chain reaction (PCR), can be used to detect the novel mRNA and may have both prognostic and diagnostic value.

The novel proteins also have value as vaccines since antibodies to them may neutralize virus infectivity. Either active or passive immunization may provide protection from HTLV-I viral infection.

The novel mRNA and/or proteins, or fragments or derivatives of them, such as antibodies to the proteins or protein fragments, may be useful as therapeutic agents since they may interfere with the normal function or reproduction of the virus.

DETAILED DESCRIPTION OF THE INVENTION

Figure 2:
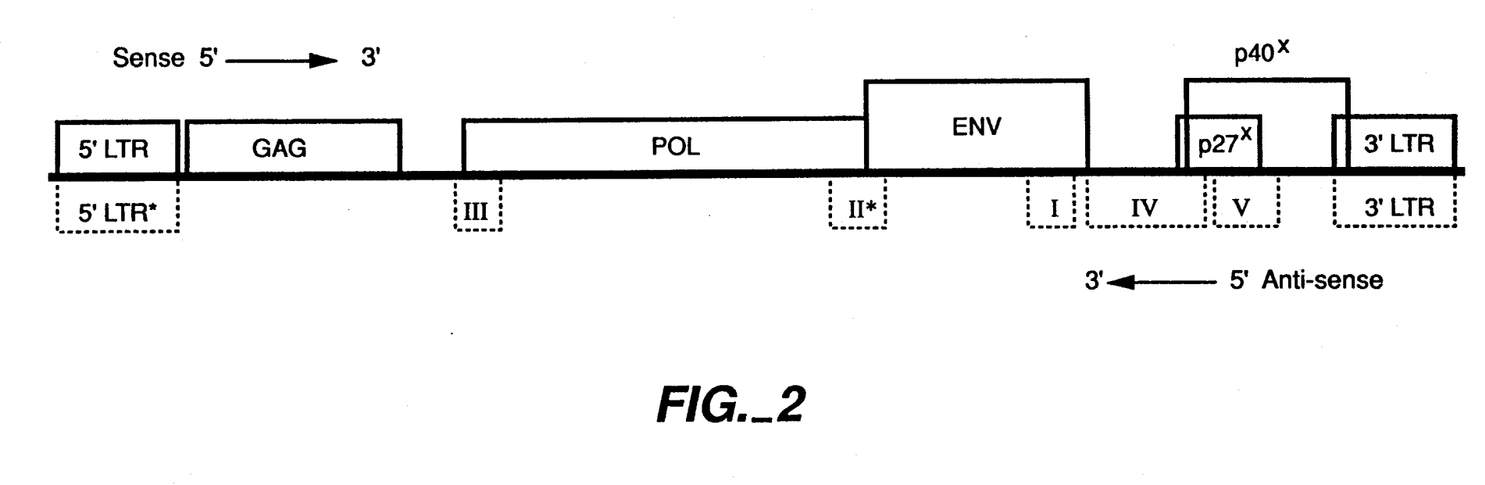
FIG. 2 shows the alignment of the sense and anti-sense DNA and the placement of the open reading frames on the anti-sense strand.

Novel polypeptides are provided which are the expression products of open reading frames found in the reverse complement of the HTLV-I viral genome found between nucleotide numbers 2473–2790, 3805–4161, 6295–6606, 1589–2383, and 1137–1544 of the anti-sense strand. The HTLV-I message which provides for translation of the novel polypeptides may contain additional nucleotides in front of and behind the sequence coding for the novel polypeptides. The nucleotide positions used for the sense strand were determined according to the numbering system of M. Seiki, S. Hattori, Y. Hirayama, and M. Yoshida, Proc. Nat. Acad. Sci. USA 80, 3618(1983). The nucleotide positions used for the anti-sense strand were derived by numbering the anti-sense nucleotide corresponding to the last nucleotide of the sense strand with the number 1. The particular polypeptides are those of molecular weight between 5KD and 100KD, preferably 5 and 50 kd, which are made of at least 50 amino acids in length and that include all or part of the following sequences I-V shown in Table 1. In addition, the invention provides novel nucleotide sequences (and silent mutations thereof) which encode the novel polypeptides as shown in Table 1. FIG. 2 shows the location of these polypeptides in the viral genome.

TABLE I (I)

| AMINO ACID SEQUENCE | Arg | Arg | Met | His | Gly | Pro | Ala | Arg | Ile | Thr |
|---|---|---|---|---|---|---|---|---|---|---|

TABLE I-continued

|  | | | | | | | | | |
|---|---|---|---|---|---|---|---|---|---|
| ANTI-SENSE mRNA (5'-3') 2473 | CGG | AGG | AUG | CAU | GGU | CCU | GCA | AGG | AUA | ACA |
| SENSE mRNA (3'-5') 6595 | GCC | UCC | UAC | GUA | CCA | GGA | CGU | UCC | UAU | UGU |
|  | Arg | Arg | Ser | Ser | Ala | Thr | Arg | Val | Ile | Pro |
|  | AGA | AGG | AGU | AGC | GCA | ACA | AGG | GUG | AUU | CCA |
|  | UCU | UCC | UCA | UCG | CGU | UGU | UCC | CAC | UAA | GGU |
|  | Val | Cys | Lys | Ala | Ser | Arg | Ala | His | Cys | Glu |
|  | GUU | UGU | AAG | GCC | UCU | CGA | GCC | CAC | UGU | GAG |
|  | CAA | ACA | UUC | CGG | AGA | GCU | CGG | GUG | ACA | CUC |
|  | Arg | Pro | Arg | Ser | Gln | Leu | Arg | Pro | Gln | Pro |
|  | AGG | CCA | AGG | UCC | CAG | UUA | AGG | CCC | CAG | CCA |
|  | UCC | GGU | UCC | AGG | GUC | AAU | UCC | GGG | GUC | GGU |
|  | Val | Arg | Thr | Arg | Phe | Ser | Arg | Gly | Gly | Leu |
|  | GUC | AGG | ACU | CGA | UUC | UCA | AGG | GGG | GGU | CUU |
|  | CAG | UCC | UGA | GCU | AAG | AGU | UCC | CCC | CCA | GAA |
|  | Ser | Cys | Ser | Ile | Gly | Thr | Trp | Glu | Leu | Val |
|  | UCU | UGU | AGU | AUU | GGG | ACA | UGG | GAA | UUG | GUA |
|  | AGA | ACA | UCA | UAA | CCC | UGU | ACC | CUU | AAC | CAU |
|  | Ile | Phe | Gly | Lys | Arg | His | Cys | Ser | Cys | Asn |
|  | AUA | UUC | GGA | AAA | CGG | CAC | UGU | UCU | UGU | AAU |
|  | UAU | AAG | CCU | UUU | GCC | GUG | ACA | AGA | ACA | UUA |
|  | Ala | Leu | His | Asn | Pro | Pro | Cys | Ser | Gln | Asn |
|  | GCU | UUG | CAU | AAU | CCU | CCU | UGC | UCC | CAG | AAC |
|  | CGA | AAC | GUA | UUA | GGA | GGA | ACG | AGG | GUC | UUG |
|  | Arg | Arg | Ser | Arg | Pro | Arg | Leu | Phe | Trp | Ala |
|  | AGG | AGA | UCA | AGG | CCU | CGU | CUG | UUC | UGG | GCA |
|  | UCC | UCU | AGU | UCC | GGA | GCA | GAC | AAG | ACC | CGU |
|  | Ala | Tyr | Cys | Ala | Ile | Leu | Ser | Arg | Phe | Leu |
|  | GCA | UAC | UGC | GCA | AUU | UUG | AGU | AGA | UUU | UUG |
|  | CGU | AUG | ACG | CGU | UAA | AAC | UCA | UCU | AAA | AAC |
|  | Trp | Phe | Leu | Thr | Ile | Ala |  |  |  |  |
|  | UGG | UUU | UUG | ACU | AUU | GCU | 2790 |  |  |  |
|  | ACC | AAA | AAC | UGA | UAA | CGA | 6278 |  |  |  |
|  | | | (II) | | | | | | | |
| AMINO ACID SEQUENCE | Ser | Pro | Lys | Met | Arg | Gly | Gln | Asn | Trp | Lys |
| ANTI-SENSE mRNA (5'-3') 3805 | UCA | CCG | AAG | AUG | AGG | GGG | CAG | AAC | UGG | AAG |
| SENSE mRNA (3'-5') 5263 | AGU | GGC | UUC | UAC | UCC | CCC | GUC | UUG | ACC | UUC |
|  | Asn | Lys | Ile | Lys | Val | Ala | Arg | Asn | Leu | Pro |
|  | AAU | AAA | AUC | AAA | GUG | GCG | AGA | AAC | UUA | CCC |
|  | UUA | UUU | UAG | UUU | CAC | CGC | UCU | UUG | AAU | GGG |
|  | Met | Val | Leu | Glu | Val | Phe | Phe | Phe | Gly | Ile |
|  | AUG | GUG | UUG | GAG | GUC | UUU | UUC | UUU | GGG | AUC |
|  | UAC | CAC | AAC | CUC | CAG | AAA | AAG | AAA | CCC | UAG |
|  | Gly | Gly | Ala | Ser | Asp | Gly | Ser | Trp | Ala | Cys |
|  | GGC | GGG | GCC | UCC | GAC | GGG | UCU | UGG | GCA | UGC |
|  | CCG | CCC | CGG | AGG | CUG | CCC | AGA | ACC | CGU | ACG |
|  | Ser | Ser | Leu | Glu | Glu | Ser | Pro | Arg | Asp | Pro |
|  | AGC | UCG | CUU | GAG | GAG | UCU | CCA | CGG | GAU | CCA |
|  | UCG | AGC | GAA | CUC | CUC | AGA | GGU | GCC | CUA | GGU |
|  | Leu | Gly | Arg | Thr | Ser | Ala | Tyr | Arg | Asp | Glu |
|  | CUG | GGC | AGA | ACU | AGC | GCU | UAC | CGG | GAU | GAG |
|  | GAC | CCG | UCU | UGA | UCG | CGA | AUG | GCC | CUA | CUC |
|  | Ser | Ser | Ala | Gly | Ser | Phe | Leu | Glu | Ser | Leu |
|  | AGC | AGC | GCC | GGC | AGC | UUC | UUG | GAG | AGC | CUC |
|  | UCG | UCG | CGG | CCG | UCG | AAG | AAC | CUC | UCG | GAG |
|  | Leu | Trp | Ser | Phe | Pro | Leu | Ala | Ala | Ile | Lys |
|  | CUG | UGG | UCC | UUU | CCA | CUG | GCG | GCU | AUU | AAG |
|  | GAC | ACC | AGG | AAA | GGU | GAC | CGC | CGA | UAA | UUC |
|  | Thr | Arg | Lys | Leu | Glu | Ile | Ile | Pro | Met | Gly |
|  | ACC | AGG | AAG | CUU | GAA | AUA | AUA | CCA | AUG | GGU |
|  | UGG | UCC | UUC | GAA | CUU | UAU | UAU | GGU | UAC | CCA |
|  | Leu | Phe | Ile | Ala | Glu | Gly | Thr | Cys | Leu | Trp |
|  | UUG | UUU | AUU | GCU | GAG | GGA | ACG | UGU | CUC | UGG |
|  | AAC | AAA | UAA | CGA | CUC | CCU | UGC | ACA | GAG | ACC |
|  | Asp | Arg | Leu | Glu | Ser | Gly | Gly | Val | Val | Lys |
|  | GAU | CGG | CUG | GAG | UCG | GGG | GGA | GUG | GUG | AAG |
|  | CUA | GCC | GAC | CUC | AGC | CCC | CCU | CAC | CAC | UUC |
|  | Leu | Pro | Ser | Gly | Phe | Val | Ala | Val | Gly |  |
|  | CUG | CCA | UCG | GGU | UUU | GUG | GCA | GUU | GGU | 4161 |
|  | GAC | GGU | AGC | CCA | AAA | CAC | CGU | CAA | CCA | 4907 |
|  | | | (III) | | | | | | | |
| AMINO ACID SEQUENCE | Arg | Val | Ser | Gly | Pro | Gln | Val | Val | Asp | Glu |
| ANTI-SENSE mRNA (5'-3') 6295 | AGA | GUU | AGU | GGC | CCG | CAG | GUC | GUG | GAU | GAA |
| SENSE mRNA (3'-5') 2773 | UCU | CAA | UCA | CCG | GGC | GUC | CAG | CAC | CUA | CUU |
|  | Ser | Pro | Gly | Ser | Ile | Gly | Leu | Phe | Asn | Trp |
|  | UCG | CCA | GGU | UCC | AUU | GGC | CUU | UUU | AAC | UGG |
|  | AGC | GGU | CCA | AGG | UAA | CCG | GAA | AAA | UUG | ACC |
|  | Glu | Tyr | Trp | Val | Ile | Pro | Trp | Pro | Gly | Val |
|  | GAA | UAC | UGG | GUU | AUU | CCC | UGG | CCC | GGU | GUA |
|  | CUU | AUG | ACC | CAA | UAA | GGG | ACC | GGG | CCA | CAU |
|  | Gly | Phe | Asp | Met | Ala | Cys | Leu | Gln | Gly | Leu |
|  | GGG | UUC | GAU | AUG | GCC | UGC | CUC | CAG | GGC | CUU |
|  | CCC | AAG | CUA | UAC | CGG | ACG | GAG | GUC | CCG | GAA |

TABLE I-continued

|  | | | | | | | | | | |
|---|---|---|---|---|---|---|---|---|---|---|
| | | Pro | Asp | Gln | Val | Leu | Gln | Gly | Leu | Glu | Ala |
| | | CCG | GAC | CAA | GUG | UUG | CAA | GGC | CUG | GAG | GCG |
| | | GGC | CUG | GUU | CAC | AAC | GUU | CCG | GAC | CUC | CGC |
| | | Phe | Trp | Phe | Lys | Gly | Asn | Trp | Leu | Ile | Ser |
| | | UUC | UGG | UUU | AAA | GGG | AAC | UGG | CUG | AUU | UCG |
| | | AAG | ACC | AAA | UUU | CCC | UUG | ACC | GAC | UAA | AGC |
| | | Gly | Gly | Leu | Gly | Arg | Cys | Ser | Ser | Pro | Arg |
| | | GGG | GGC | CUU | GGG | AGG | UGU | UCU | AGC | CCA | AGG |
| | | CCC | CCG | GAA | CCC | UCC | ACA | AGA | UCG | GGU | UCC |
| | | Thr | Ala | Gly | Ala | Cys | Ile | Gly | Lys | Ile | Thr |
| | | ACG | GCU | GGC | GCC | UGU | AUU | GGC | AAG | AUU | ACA |
| | | UGC | CGA | CCG | CGG | ACA | UAA | CCG | UUC | UAA | UGU |
| | | Gly | Gly | Leu | Phe | Ala | Ser | Gly | Arg | Tyr | Arg |
| | | GGC | GGC | CUU | UUU | GCC | UCA | GGG | AGG | UAC | AGG |
| | | CCG | CCG | GAA | AAA | CGG | AGU | CCC | UCC | AUG | UCC |
| | | Thr | Pro | Trp | His | Cys | Cys | Lys | Ala | Ser | Arg |
| | | ACG | CCU | UGG | CAU | UGU | UGU | AAG | GCA | UCA | CGA |
| | | UGC | GGA | ACC | GUA | ACA | ACA | UUC | CGU | AGU | GCU |
| | | Pro | Met | Met | Ala | | | | | | |
| | | CCU | AUG | AUG | GCC | 6606 | | | | | |
| | | GGA | UAC | UAC | CGG | 2462 | | | | | |
| | | | | (IV) | | | | | | | |
| AMINO ACID SEQUENCE | | Ser | Asp | Ala | Leu | Asp | Arg | Trp | Pro | Val | Gly |
| ANTI-SENSE mRNA (5'-3') | 1589 | UCU | GAU | GCU | CUG | GAC | AGG | UGG | CCA | GUA | GGG |
| SENSE mRNA (3'-5') | 7479 | AGA | CUA | CGA | GAC | CUG | UCC | ACC | GGU | CAU | CCC |
| | | Arg | Asp | Asp | Val | Gly | Gly | Pro | Asn | Ile | Val |
| | | CGU | GAC | GAU | GUA | GGC | GGG | CCG | AAC | AUA | GUC |
| | | GCA | CUG | CUA | CAU | CCG | CCC | GGC | UUG | UAU | CAG |
| | | Pro | Gln | Arg | Trp | Gly | Thr | Ser | Arg | Leu | Val |
| | | CCC | CAG | AGA | UGG | GGC | ACC | AGU | CGC | CUU | GUA |
| | | GGG | GUC | UCU | ACC | CCG | UGG | UCA | GCG | GAA | CAU |
| | | His | Ser | Leu | Gln | Thr | Arg | Arg | Leu | Gly | Ile |
| | | CAC | AGU | CUC | CAA | ACA | CGU | AGA | CUG | GGU | AUC |
| | | GUG | UCA | GAG | GUU | UGU | GCA | UCU | GAC | CCA | UAG |
| | | Arg | Lys | Glu | Asp | Ser | Val | Gln | Thr | Leu | Gly |
| | | CGA | AAA | GAA | GAC | UCU | GUC | CAA | ACC | CUG | GGA |
| | | GCU | UUU | CUU | CUG | AGA | CAG | GUU | UGG | GAC | CCU |
| | | Ser | Gly | Leu | Ile | Ile | Ser | Met | Val | Asn | Phe |
| | | AGU | GGG | CUG | AUA | AUA | AGC | AUG | GUU | AAC | UUU |
| | | UCA | CCC | GAC | UAU | UAU | UCG | UAC | CAA | UUG | AAA |
| | | Val | Ser | Ala | Gly | Leu | Phe | Arg | Cys | Leu | Pro |
| | | GUA | UCU | GCA | GGG | CUG | UUU | CGA | UGC | UUG | CCU |
| | | CAU | AGA | CGU | CCC | GAC | AAA | GCU | ACG | AAC | GGA |
| | | Val | Ser | Cys | Pro | Glu | Asp | Leu | Leu | Val | Glu |
| | | GUG | UCA | UGC | CCG | GAG | GAC | CUG | CUG | GUG | GAG |
| | | CAC | AGU | ACG | GGC | CUC | CUG | GAC | GAC | CAC | CUC |
| | | Glu | Leu | Val | Asp | Gly | Leu | Leu | Ser | Leu | Glu |
| | | GAA | UUG | GUG | GAC | GGG | CUA | UUA | UCC | UUG | GAG |
| | | CUU | AAC | CAC | CUG | CCC | GAU | AAU | AGG | AAC | CUC |
| | | Glu | Glu | Leu | Lys | Asp | Lys | Glu | Glu | Glu | Glu |
| | | GAA | GAG | UUA | AAG | GAC | AAG | GAG | GAG | GAG | GAA |
| | | CUU | CUC | AAU | UUC | CUG | UUC | CUC | CUC | CUC | CUU |
| | | Ala | Val | Leu | Asp | Gly | Leu | Leu | Ser | Leu | Glu |
| | | GCU | GUG | CUU | GAC | GGU | UUG | CUA | UCC | UUA | GAA |
| | | CGA | CAC | GAA | CUG | CCA | AAC | GAU | AGG | AAU | CUU |
| | | Glu | Glu | Ser | Arg | Gly | Arg | Leu | Arg | Arg | Gly |
| | | GAG | GAA | AGC | CGC | GGC | CGG | CUG | CGA | CGG | GGC |
| | | CUC | CUU | UCG | GCG | CCG | GCC | GAC | GCU | GCC | CCG |
| | | Pro | Pro | Gly | Glu | Lys | Ala | Pro | Pro | Arg | Gly |
| | | CCU | CCA | GGG | GAG | AAA | GCG | CCA | CCU | CGC | GGG |
| | | GGA | GGU | CCC | CUC | UUU | CGC | GGU | GGA | GCG | CCC |
| | | Glu | Thr | His | Arg | Asp | Arg | Gln | Arg | Arg | Ala |
| | | GAA | ACG | CAU | CGU | GAU | CGG | CAG | CGA | CGG | GCU |
| | | CUU | UGC | GUA | GCA | CUA | GCC | GUC | GCU | GCC | CGA |
| | | Glu | Glu | Lys | Arg | Lys | Arg | Lys | Lys | Glu | Arg |
| | | GAG | GAG | AAG | AGG | AAG | CGA | AAA | AAA | GAG | CGG |
| | | CUC | CUC | UUC | UCC | UUC | GCU | UUU | UUU | CUC | GCC |
| | | Glu | Lys | Glu | Glu | Glu | Gln | Thr | Ala | Glu | |
| | | GAG | AAA | GAG | GAG | GAA | AAG | CAG | ACC | GCU | GAG |
| | | CUC | UUU | CUC | CUC | CUU | UUC | GUC | UGG | CGA | CUC |
| | | Tyr | Leu | Lys | Arg | Lys | Glu | Glu | Glu | Lys | Ala |
| | | UAU | UUG | AAA | AGG | AAG | GAA | GAG | GAG | AAG | GCA |
| | | AUA | AAC | UUU | UCC | UUC | CUU | CUC | CUC | UUC | CGU |
| | | Arg | Arg | Arg | Arg | Arg | Ala | Glu | Lys | Lys | Ala |
| | | CGG | CGC | AGG | AGG | CGG | GCG | GAG | AAG | AAG | GCC |
| | | GCC | GCG | UCC | UCC | GCC | CGC | CUC | UUC | UUC | CGG |
| | | Ala | Asp | Val | Ala | Arg | Arg | Lys | Gln | Glu | Glu |
| | | GCU | GAC | GUC | GCU | AGG | AGG | AAG | CAG | GAA | GAG |
| | | CGA | CUG | CAG | CGA | UCC | UCC | UUC | GUC | CUU | CUC |
| | | Gln | Glu | Arg | Arg | Glu | Arg | Lys | Trp | Arg | Gln |
| | | CAG | GAG | CGC | CGU | GAG | CGC | AAG | UGG | AGA | CAA |
| | | GUC | CUC | GCG | GCA | CUC | GCG | UUC | ACC | UCU | GUU |

TABLE I-continued

|  | Gly | Ala | Glu | Lys | Ala | Lys | Gln | His | Ser | Ala |
|---|---|---|---|---|---|---|---|---|---|---|
|  | GGG | GCU | GAG | AAG | GCG | AAA | CAG | CAU | AGU | GCU |
|  | CCC | CGA | CUC | UUC | CGC | UUU | GUC | GUA | UCA | CGA |
|  | Arg | Lys | Glu | Lys | Met | Gln | Glu | Leu | Gly | Ile |
|  | AGG | AAA | GAA | AAA | AUG | CAG | GAG | UUG | GGG | AUU |
|  | UCC | UUU | CUU | UUU | UAC | GUC | CUC | AAC | CCC | UAA |
|  | Asp | Gly | Tyr | Thr | Arg | Gln | Leu | Glu | Gly | Glu |
|  | GAU | GGC | UAU | ACU | AGA | CAG | UUG | GAA | GGC | GAG |
|  | CUA | CCG | AUA | UGA | UCU | GUC | AAC | CUU | CCG | CUC |
|  | Val | Glu | Ser | Leu | Glu | Ala | Glu | Arg | Arg | Lys |
|  | GUG | GAG | UCC | UUG | GAG | GCU | GAA | CGG | AGG | AAG |
|  | CAC | CUC | AGG | AAC | CUC | CGA | CUU | GCC | UCC | UUC |
|  | Leu | Leu | Gln | Glu | Lys | Glu | Asp | Leu | Met | Gly |
|  | UUG | CUG | CAG | GAG | AAG | GAG | GAU | UUG | AUG | AGG |
|  | AAC | GAC | GUC | CUC | UUC | CUC | CUA | AAC | UAC | CCU |
|  | Glu | Val | Asn | Tyr | Trp | Gln | Gly | Arg | Leu | Glu |
|  | GAG | GUU | AAU | UAU | UGG | CAG | GGG | AGG | CUG | GAG |
|  | CUC | CAA | UUA | AUA | ACC | GUC | CCC | UCC | GAC | CUC |
|  | Ala | Met | Trp | Leu | Gln |  |  |  |  |  |
|  | GCG | AUG | UGG | UUG | CAA | 2383 |  |  |  |  |
|  | CGC | UAC | ACC | AAC | GUU | 6685 |  |  |  |  |

(V)

|  | Gly | Pro | Cys | Gly | Glu | Gly | Asn | Phe | Ile | Glu |
|---|---|---|---|---|---|---|---|---|---|---|
| AMINO ACID SEQUENCE | | | | | | | | | | |
| ANTI-SENSE mRNA (5'-3') 1137 | GGC | CCC | UGU | GGU | GAG | GGA | AAU | UUU | AUA | GAG |
| SENSE mRNA (3'-5') 7931 | CCG | GGG | ACA | CCA | CUC | CCU | UUA | AAA | UAU | CUC |
|  | Glu | Phe | Phe | Tyr | Ser | Leu | Val | Gly | Asn | Ile |
|  | GAG | UUC | UUC | UAU | UCG | CUU | GUA | GGG | AAC | AUU |
|  | CUC | AAG | AAG | AUA | AGC | GAA | CAU | CCC | UUG | UAA |
|  | Gly | Glu | Glu | Gly | Pro | Glu | Leu | Ala | Gly | Val |
|  | GGU | GAG | GAA | GGC | CCC | GAG | CUG | GCC | GGG | GUG |
|  | CCA | CUC | CUU | CCG | GGG | CUC | GAC | CGG | CCC | CAC |
|  | Ala | Lys | Asn | His | Val | Gly | Gln | Glu | Gly | Pro |
|  | GCA | AAA | AAU | CAC | GUG | GGG | CAG | GAG | GGG | CCA |
|  | CGU | UUU | UUA | GUG | CAC | CCC | GUC | CUC | CCC | GGU |
|  | Gly | Asp | Gly | Gly | Gly | Lys | Leu | Val | Glu | Val |
|  | GGU | GAU | GGG | GGG | GGA | AAG | CUG | GUA | GAG | GUA |
|  | CCA | CUA | CCC | CCC | CCU | UUC | GAC | CAU | CUC | CAU |
|  | His | Ala | Asp | Asn | Gly | Ala | Ser | Pro | Glu | Gly |
|  | CAU | GCA | GAC | AAC | GGA | GCC | UCC | CCA | GAG | GGU |
|  | GUA | CGU | CUG | UUG | CCU | CGG | AGG | GGU | CUC | CCA |
|  | Val | Gln | Val | Leu | Gly | Pro | Glu | Ser | Gly | Val |
|  | GUA | CAG | GUU | UUG | GGG | CCG | GAG | UCC | GGG | GUC |
|  | CAU | GUC | CAA | AAC | CCC | GGC | CUC | AGG | CCC | CAG |
|  | Trp | Lys | Arg | Gln | Gly | Trp | Glu | Val | Leu | Pro |
|  | UGG | AAA | AGA | CAG | GGU | UGG | GAG | GUG | CUG | CCC |
|  | ACC | UUU | UCU | GUC | CCA | ACC | CUC | CAC | GAC | GGG |
|  | Lys | Gly | Gly | Phe | His | Val | Ser | Ile | Ser | Glu |
|  | AAG | GGU | GGG | UUC | CAU | GUA | UCC | AUU | UCG | GAA |
|  | UUC | CCA | CCC | AAG | GUA | CAU | AGG | UAA | AGC | CUU |
|  | Gly | Gly | Val | Phe | Ala | His | Gly | Leu | Glu | Glu |
|  | GGG | GGA | GUA | UUU | GCG | CAU | GGC | CUG | GAG | GAA |
|  | CCC | CCU | CAU | AAA | CGC | GUA | CCG | GAC | CUC | CUU |
|  | Gly | Gly | Trp | Asn | Val | Gly | Gly | Cys | Met | Ser |
|  | GGA | GGG | UGG | AAU | GUU | GGG | GGU | UGU | AUG | AGU |
|  | CCU | CCC | ACC | UUA | CAA | CCC | CCA | ACA | UAC | UCA |
|  | Asp | Trp | Arg | Gly | Lys | Asp | Leu | Glu | Gly | Leu |
|  | GAU | UGG | CGG | GGU | AAG | GAC | CUU | GAG | GGU | CUU |
|  | CUA | ACC | GCC | CCA | UUC | CUG | GAA | CUC | CCA | GAA |
|  | Arg | Gly | Ser | Leu | Gly | Gly | Glu | Gly | Gly | Glu |
|  | AGA | GGU | UCU | CUG | GGU | GGG | GAA | GGA | GGG | GAG |
|  | UCU | CCA | AGA | GAC | CCA | CCC | CUU | CCU | CCC | CUC |
|  | Ser | Arg | Asp | Lys | Glu | Leu |  |  |  |  |
|  | UCG | AGG | GAU | AAG | GAA | CUG | 1544 |  |  |  |
|  | AGC | UCC | CUA | UUC | CUU | GAC | 7524 |  |  |  |

The polypeptides of this invention can be made entirely of one of the above sequences or of parts of more than one of the above sequences. The novel peptides of this invention also include peptide fragments of 10 or more amino acids taken from any of the above peptide sequences. The message which is translated into these polypeptides may contain additional nucleotides from the anti-sense strand which may be necessary for translation but are not translated into the resultant polypeptide, peptide, or protein. For example, the message responsible for translation of polypeptides from sequences I, IV, and V above, begins near nucleotide 918 of the anti-sense strand of the HTLV-I virus.

The above polypeptides and peptides can be used as immunogens for the production of antisera or monoclonal antibodies specific for the particular polypeptide or peptide and as reagents to detect antibodies generated in response to infection with the HTLV-I virus.

To be useful in the detection methods of the invention, the polypeptides or peptides of the invention are suitably obtained in substantially pure form, that is, typically about 50% w/w or more purity, substantially free of interfering proteins and contaminants. Preferably, these polypeptides or peptides are isolated or synthesized in a purity of at least about 80% w/w and, more preferably, in at least about 95% w/w purity, being substantially free of other proteins from humans, viral proteins, or other contaminants. Using conventional protein purification techniques. homogeneous polypeptides and peptides of at least about 99% w/w can be obtained and these homogeneous polypeptides and peptides are most desirably used in the methods of the invention. The polypeptides and peptides of the invention can also be obtained in substantially pure form by use of the antibodies herein described in immunoabsorbant affinity chromatography. This immunoabsorbant affinity chromatography is carried out by first linking the antibodies to a solid support and then contacting the linked antibodies with lysates of cells infected with the HTLV-I virus or lysates or supernatants of cells producing the peptides or polypeptides as a result of DNA techniques described below. Peptides and polypeptides obtained in this manner are also within the scope of this invention and can be used in the methods of the invention to detect the presence of HTLV-I or its products.

The peptides of the present invention can be prepared by conventional processes for synthesizing peptides; more specifically, using processes as described in Schroder and Lubke, *The Peptides*, Vol. 1, published by Academic Press, New York (1966), or Izumiya, et al., *Synthesis of Peptides*, published by Maruzen Publishing Co., Ltd., (1975), both of which are herein incorporated by reference. For example, an azide process, an acid chloride process, an acid anhydride process, a mixed anhydride process an active ester process (for example: p-nitrophenyl ester, N-hydroxysuccinimide ester, or cyanomethyl ester), a carbodiimidazole process, an oxidative-reductive process, or a DCC/additive process can be used. Solid phase and solution phase syntheses are both applicable to the foregoing processes.

The peptides of the present invention are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. (Amino groups that are not being used in the coupling reaction must be protected to prevent coupling at an incorrect location.)

In case a solid phase synthesis is adopted, the C-terminal amino acid is bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin; hydroxymethyl resins, phenol resins, tert-alkyloxycarbonyl-hydrazidated resins, and the like.

An amino group-protected amino acid is bound in sequence through condensation of its reactive amino group and the reactive carboxyl group, in sequence, to synthesize step by step. After synthesizing the complete sequence, the peptide is split off from the insoluble carrier to produce the peptide. This solid-phase approach is generally described by Merrifield, et al. in *J. Am. Chem. Soc.*, 85, 2149-2156 (1963), which is herein incorporated by reference.

The peptides of this invention can also be prepared through recombinant DNA techniques. The amino acid sequence of the desired peptide is used to deduce the codon sequence for the single-stranded DNA. synthesized using conventional synthetic techniques or the natural gene is isolated by cDNA cloning (including multiple gene copy techniques), then the double-stranded DNA is prepared and inserted at a suitable site in a cloning vehicle, vector, or plasmid. An appropriate organism, such as bacteria cells, yeast cells, or mammalian cells, is transformed to obtain expression of the desired peptide.

The prepared peptides of the present invention can be isolated and purified from the reaction mixture by means of peptide separation, for example, by extraction, counter-current distribution, column chromatography, high performance liquid chromatography, and the like.

The peptides of this invention form salts with a variety of inorganic or organic bases. The non-toxic, pharmaceutically-acceptable salts are preferred, although other salts are also useful in isolating or purifying the product. Such pharmaceutically-acceptable salts include metal salts, such as sodium, potassium, or lithium, alkaline earth metal salts, such as calcium or magnesium, and salts derived from amino acids, such as arginine or lysine. The salts are obtained by reacting the acid form of the peptide with an equivalent of the base supplying the desired ion in a medium in which the salt precipitates or in aqueous medium and then lyophilizing.

Similarly, the peptides form salts with a variety of inorganic and organic acids. Again, the non-toxic, pharmaceutically-acceptable salts are preferred, although other salts are also useful in isolating or purifying the product. Such pharmaceutically acceptable salts include those formed with hydrochloric acid, methanesulfonic acid, sulfuric acid, maleic acid, and the like. The salts are obtained by reacting the product with an equivalent amount of the acid in a medium in which the salt precipitates.

The polypeptides greater than about 30 amino acids, particularly greater than about 50 amino acids may serve as immunogens to produce the antibodies of the present invention. If the polypeptides are less than about 1000D, particularly less than about 600D, they may be joined to other materials, particularly polypeptides, as fused or covalently joined polypeptides to be used as immunogens. The subject polypeptides may be fused or covalently linked to a variety of immunogens, such as keyhole limpet hemocyanin, bovine serum albumin, tetanus toxoid, etc. See for example, *Microbiology*, Hoeber Medical Division, Harper and Row, 1969; Landsteiner, *Specificity of Serological Reactions*. Dover Publications, New York, 1962, and Williams et al., *Methods in Immunology and Immunochemistry*, Vol. 1, Academic Press, New York, 1967, for descriptions of preparation of polyclonal antisera. In many instances, it will be desired to prepare monoclonal antibodies, where the monoclonal antibodies may be from various mammalian hosts, such as mice, rodents, primates, humans, etc. Description of techniques for preparing monoclonal antibodies may be found in, *Basic and Clinical Immunology*, Stites et al., Eds., Fourth edition, Lange Medical Publications, Los Altos, Calif. and references cited therein.

These antibodies can be used in various ways, depending upon whether they are polyclonal or monoclonal. The polyclonal antibodies can be used to detect polypeptides having the epitopic site(s) associated with the polypeptides or proteins expressed by the open reading frames found on the "anti-sense" strand of the HTLV-I virus. Thus, they can detect the presence of any polypeptide which shares one or more epitopic sites of the subject polypeptides. The monoclonal antibodies, by way of contrast, can detect specific sites or can be used in conjunction to demonstrate the presence of more than one specific epitopic site. Thus, the monoclonal antibodies provide for greater specificity as to a specific epitopic site or sites present on the same or different polypeptides.

The subject polypeptides, peptides, their fusion products, and antibodies specific for the polypeptides and peptides find use in a variety of diagnostics for detecting the presence of HTLV-I virus. This can be done by employing lysates, fixing cells and employing immunofluorescence, detecting the presence of related antibodies or antigens in serum, or the like.

The polypeptides, peptides, and/or antibodies may be used without modification or may be modified in a variety of ways, for example, by labelling. By labelling is intended joining, either covalently or non-covalently, a moiety which directly or indirectly provides for detectable signal. A wide variety of labels are known and have found extensive use in both the scientific and patent literature. These labels include radionuclides, enzymes, substrates, cofactors, inhibitors, fluorescers, chemiluminescers, particles, magnetic particles, and the like. Illustrative patents include U.S. Pat. Nos. 3,817,837, 3,850,752, 3,939,350, 3,996,345, 4,277,437, 4,275,149 and 4,366,241, which are merely illustrative of various techniques which are available.

The manners for linking the polypeptides and peptides to the various labels have been extensively reported in the literature and do not require extensive exemplification here. Many of the techniques involve the use of activated carboxyl groups, either through the use of carbodiimide or active esters to form peptide bonds; the formation of thioethers by reaction of a mercapto group with an activated halogen, e.g., chloroacetyl, or activated olefin, e.g., maleimide, for linkage, or the like.

The assays may be homogeneous (without a separation step between free reagent and receptor-ligand complex) or heterogeneous (with a separation step between free reagent and receptor-ligand complex). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLIFA) and the like.

Unlabelled antibodies can be employed by employing a second antibody which is labelled which recognizes the antibody to a subject polypeptide. These assays have also found extensive exemplification in the literature.

Antibodies to any of the peptides of the invention may be used to detect polypeptides of the HTLV-I virus sharing common epitopic sites. In addition, by employing techniques which allow for molecular weight discrimination, e.g., immunoprecipitation followed by SDS page, the nature of the polypeptide or peptide and, therefore, the virus may be further characterized.

Frequently, the reagents are supplied in kits, so as to optimize the sensitivity of the assay. For the subject invention, depending upon the nature of the assay, the protocol, and the label, either labelled or unlabeled antibody, or labelled polypeptide is provided, usually in conjunction with other additives, such as buffer, stabilizers, materials necessary for signal production, e.g., substrates for enzymes, and the like. Desirably, the reagents are provided as a dry powder, where the reagents may be reconstituted in an aqueous medium having appropriate concentrations for performing the assay.

The antibodies can also be used for affinity chromatography in isolating the polypeptides produced by HTLV-I or analogous polypeptides. Columns can be prepared where the antibodies are linked to a solid support, e.g., particles, such as agarose, Sephadex, or the like, where a cell lysate may be passed through the column, the column washed, followed by increasing concentrations of a mild denaturant, e.g., urea, whereby the purified proteins will be released.

Oligonucleotide and polynucleotide sequences taken from line 3 labeled "SENSE mRNA (3'-5')" of Table 1 above or taken from 5228 to 8145 of the viral RNA and the corresponding DNA sequences may also be used as probes for detecting the level of production of novel anti-sense mRNA in cells suspected of being HTLV-I infected. The preparation of both RNA and DNA nucleotide sequences, the labeling of the sequences and the preferred size of the sequences has received ample description and exemplification in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}P$. However, other techniques may also be employed, such as using biotin modified nucleotides for introduction into a polynucleotide. The biotin then serves as the site for binding to avidin or antibodies, which may be labelled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labelled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT) and hybrid arrested translation (HART). This also includes amplification techniques such as polymerase chain reaction (PCR).

When used as vaccines, the novel proteins or polypeptides of this invention may be administered directly to the host to be immunized or depending on the size of the protein or polypeptides, it may be desirable to conjugate them to carrier proteins such as ovalbumin or serum albumin prior to their administration. The vaccine composition will include an immunogenic amount of the polypeptide, a parenteral vehicle, and, optionally, an immunopotentiator. The vaccine will be administered parenterally.

Therapeutic formulations of the novel RNA and/or peptides or polypeptides, or fragments or derivatives may be administered in any conventional dosage formulation. While it is possible for the active ingredient to be administered alone, it is preferable to present it as a pharmaceutical formulation. Formulations comprise at least one active ingredient as defined above together with one or more acceptable carriers thereof and optionally other therapeutic agents. Each carrier must be "acceptable" in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy.

EXAMPLE 1

Peptide Synthesis

Reagents used in peptide synthesis were purchased from the indicated vendors: Boc amino acids, Peninsula Laboratories, Belmont, Calif.; diisopropylcarbodiimide and 1-hydroxybenzotriazole, Aldrich, Milwaukee, Wis.; carbon-14 labelled amino acids, New England Nuclear.

All peptides were synthesized according to established Merrifield solid phase synthetic procedure (Erickson et al., (1976) Proteins -2, pp 256-527 and Stewart et al., (1984) Solid Phase Synthesis Pierce Chemical Co. Rockford IL) using an automated instrument, Model 9500, from Biosearch (San Rafael, Calif.). The first amino acid. i.e., the carboxy terminal residue, was esterified to choloromethylated polystyrene-divinylbenzene coploymer (Bio-Rad, 1% cross-linked, 1.34 milli-equivalents/g) as described previously in Hoeprich and Doolittle (1983) Biochemistry 22, pp 2049. Subsequent amino acids were coupled twice using diisopropylcarbodiimide as a coupling agent. In general, the Boc group was removed by treating the protected peptide resin for 20 min with 45% trifluoroacetic acid in dichloromethane (v/v), followed by two 5 min neutralizations with 5% diisopropylethylamine in dichloromethane (v/v). The resin was washed before and after each deprotection, neutralization and coupling step with appropriate solvents. Boc group removal and completeness of coupling was monitored qualitatively by a ninhydrin color test (Kaiser et al., (1970) Anal. Biochem. 34, pp 595). Carbon-14 containing amino acids, e.g., glycine, were coupled initially through a diisopropylcarbodiimide mediated reaction and secondly by utilizing a preformed 1-hydroxybenzotriazole ester.

All peptides were cleaved from the resin with simultaneous side-chain protecting group removal by exposure to anhydrous hydrogen fluoride for 40 min at 0°-4° C. in the presence of 10% anisole (v/v). After removal of hydrogen fluoride by water aspiration, the resin was washed with anhydrous ethyl ether to remove the anisole. The peptide was washed from the resin with sequential washes of dimethylformamide, 50% dimethylformamide/ 10% acetic acid, 10% acetic acid and distilled water; the combined washings were lyophilized.

Purification of the peptides was accomplished by reverse-phase high performance liquid chromatography (HPLC). Using a preparative column (Whatman, Partisil 10 ODS-3 Magnum 20, 2.2×50 cm), the desired peptide was eluted during gradient development of the chromatogram; the elution program ranged from 83% solvent A (0.05% trifluoroacetic acid/acetonitrile) to 50% A and 50%B over 65 minutes. A portion of each purified peptide was hydrolyzed in 6.0N HCL (Pierce) using a Waters "Pico-Tag" work station. Amino acid compositions were obtained by precolumn derivatization with 0-phthalaldehyde followed by quantitative resolution on reverse-phase HPLC (Henrikson and Meredith (1984) Anal. Biochem. 136 pp 65-74). In this way, peptides corresponding to amino acid residues 23-42, 95-112, and 167-184 or polypeptide IV (Table 1) were prepared.

EXAMPLE 2

Anti-Sense Transcription Occurring In a Retrovirus

Figure 3A:
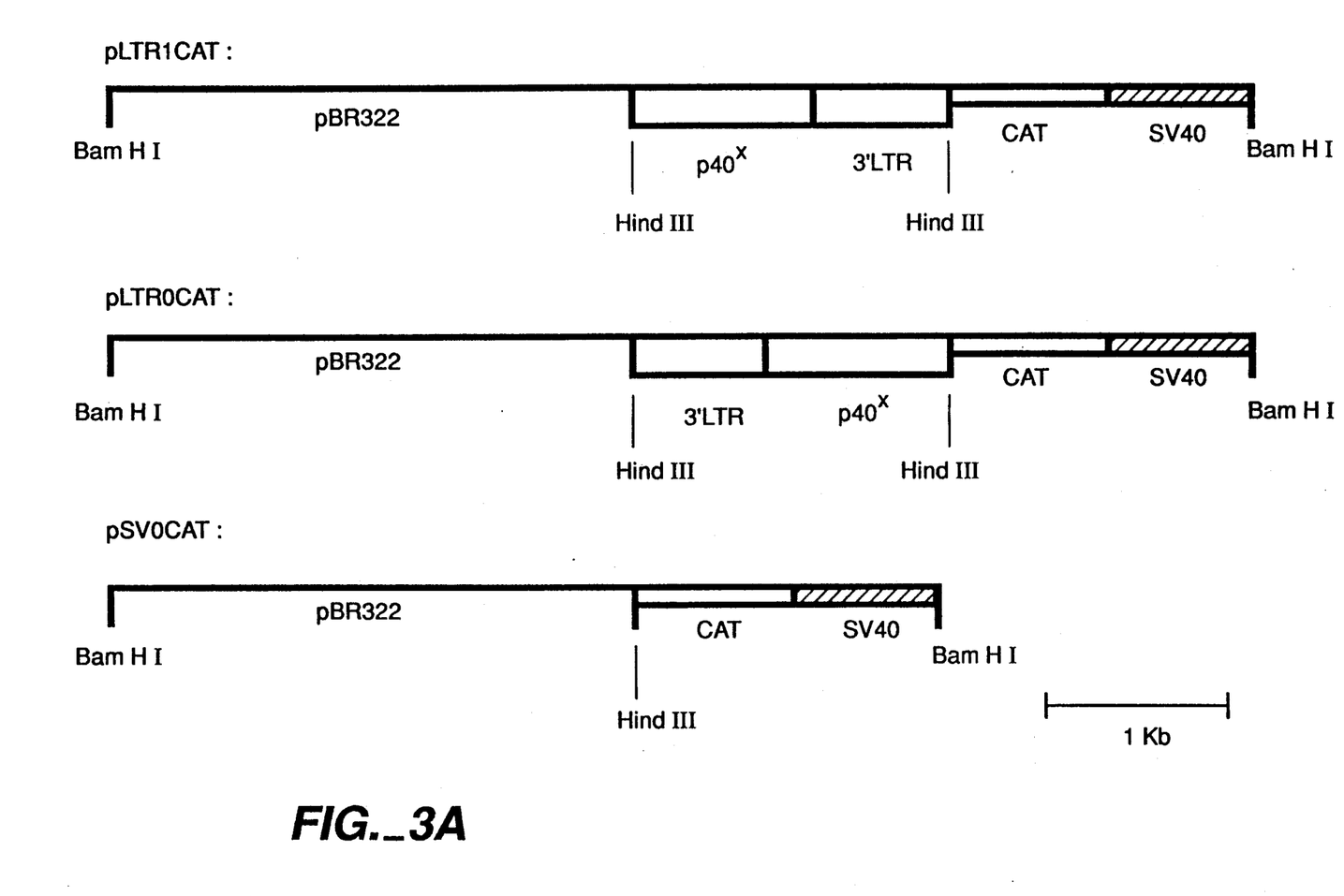
FIG. 3 shows HTLV-I anti-sense strand DNA directed CAT expression in transfected HeLa cells.

It is known that the sense strand promoter in the 3' LTR of HTLV-I can drive CAT (chloramphenicol acetyltransferase) gene expression when fused to the CAT gene in the plasmid pLTRlCAT. See A. J. Cann, J. D. Rosenblatt, W. Wachsman, N. P. Shah, and I. S. Y. Chen, Nature(London) 318, 571(1985). I. S. Y. Chen et al., Science 229, 54(1985). To test for anti-sense promotion, the orientation of the 3' LTR and flanking p40x sequences were reversed in the plasmid pLTRICAT to make pLTROCAT (FIG. 3A). The promoterless CAT expression plasmid pSVOCAT was tested as a negative control. PSVOCAT was constructed by deleting the HTLV-I sequences in pLTRlCAT and is therefore identical to the pSVOCAT described by C. M. Gorman, L. F. Moffat, and B. H. Howard, Mol. Cell. Biol. 2, 1044(1982). In this system, CAT activity has been shown to be an indication of promoter strength. If there is an active promoter on the anti-sense strand in pLTROCAT, it is expected that transcription would continue into the CAT gene sequences resulting in CAT activity in transiently transfected cells. The CAT gene in pLTROCAT is in about the same position (to within 100 bases) relative to the 3' LTR as the first methionine codon of orf-IV (see FIG. 2) in the anti-sense viral RNA.

Figure 3B:
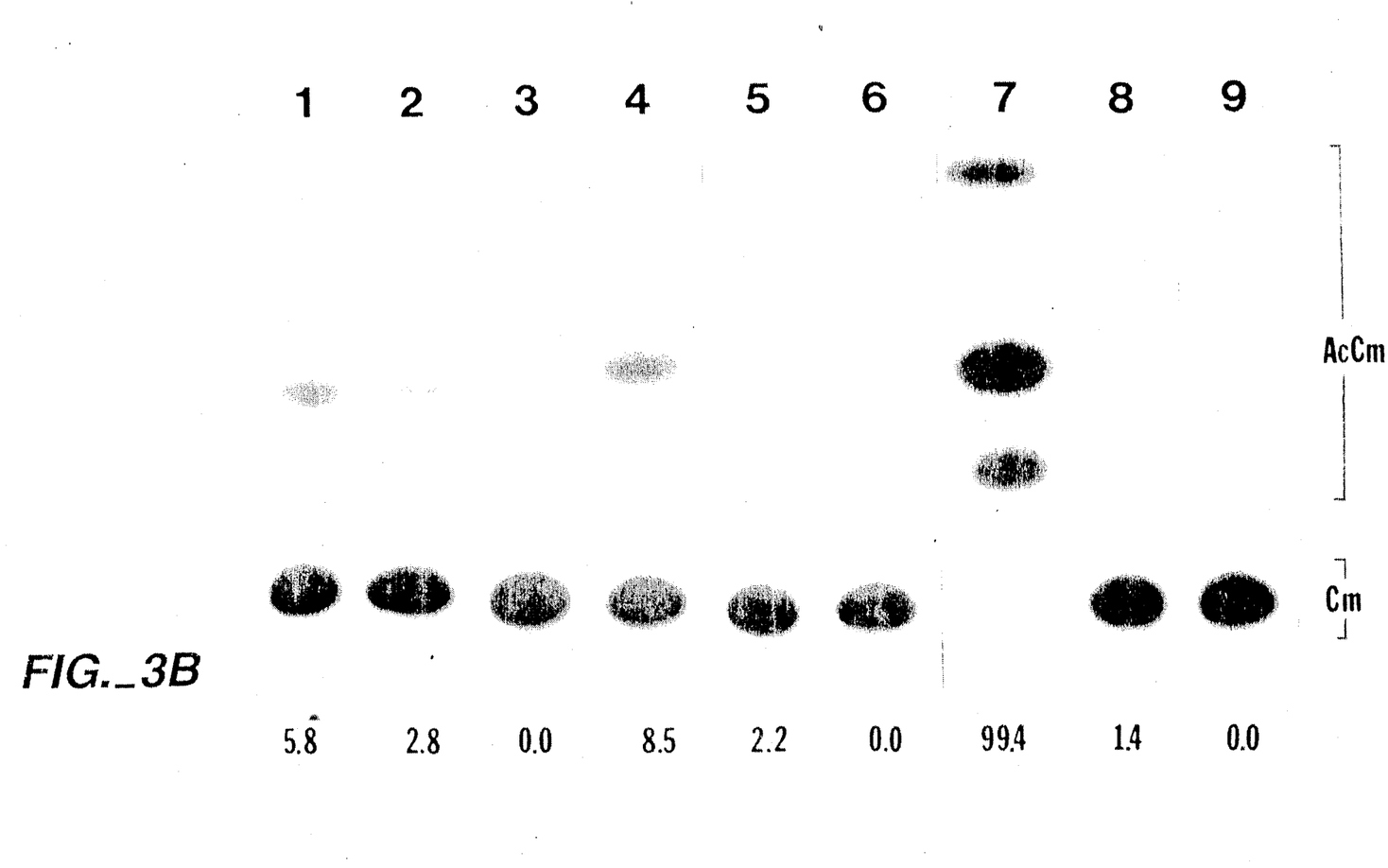

We tested three plasmids by cotransfection with either a vector plasmid (PUC19), a p40x expression plasmid (pSVMTEXΔX), or a non-functional, frameshift mutant of pSVMTEXΔX (pSVMTEXΔXC) in HeLa cells. The p40x expression plasmid pSVMTEXΔX was constructed by inserting the mouse metallothionine promoter 5' to an envelope/pX cDNA (provided by Dennis Slamon, UCLA) that was cloned into a pCD-derived cDNA cloning vector (H. Okayama and P. Berg, Mol. Cell Biol. 5, 1136(1985). The sequences between the two Xho I sites in the envelope gene were deleted. The frameshift mutated pX expression plasmid, pSVMTEXΔXC, was constructed by Cla 1 digestion, Klenow treatment, and ligation of pSVMTEXΔX resulting in a 2 base pair insertion at the 5' end of the p40x reading frame. The resulting CAT assays are shown in FIG. 3B. As others have shown, pLTRlCAT is transactivated in the presence of p40x resulting in high CAT expression and has a low basal level of CAT expression in the presence of the vector control or the mutated p40x (FIG. 3B, lanes 1. 4. and 7). PLTROCAT also shows a similar low level of expression with the vector control and mutant p40x vector, but unlike pLTRICAT, is not transactivated by p40x (FIG. 3B, lanes 2, 5, and 8). Transfection with pSVOCAT consistently gave no CAT activity (FIG. 3B, lanes 3, 6, and 9), indicating that there are no promoters in the non-HTLV-I sequences of pLTROCAT. It can be concluded from these data that there is a promoter in the anti-sense strand of the 3' 1.8 kilobases (Kb) terminus of HTLV-I.

EXAMPLE 3

Detection of HTLV-I Anti-Sense mRNA

In HTLV-I Infected Cell Line

Figure 4A:
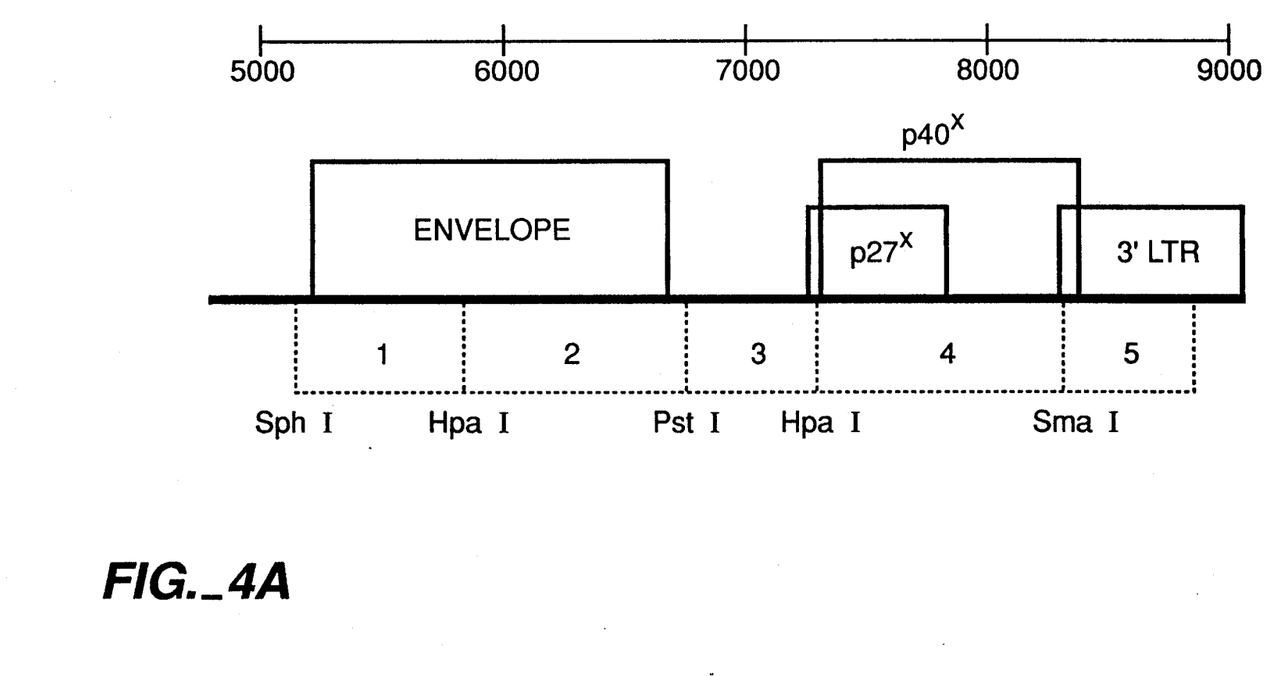
FIG. 4 shows the RNA blot analysis of HTLV-I anti-sense RNA from Molt4 and SLBl cells.
Figure 4B:
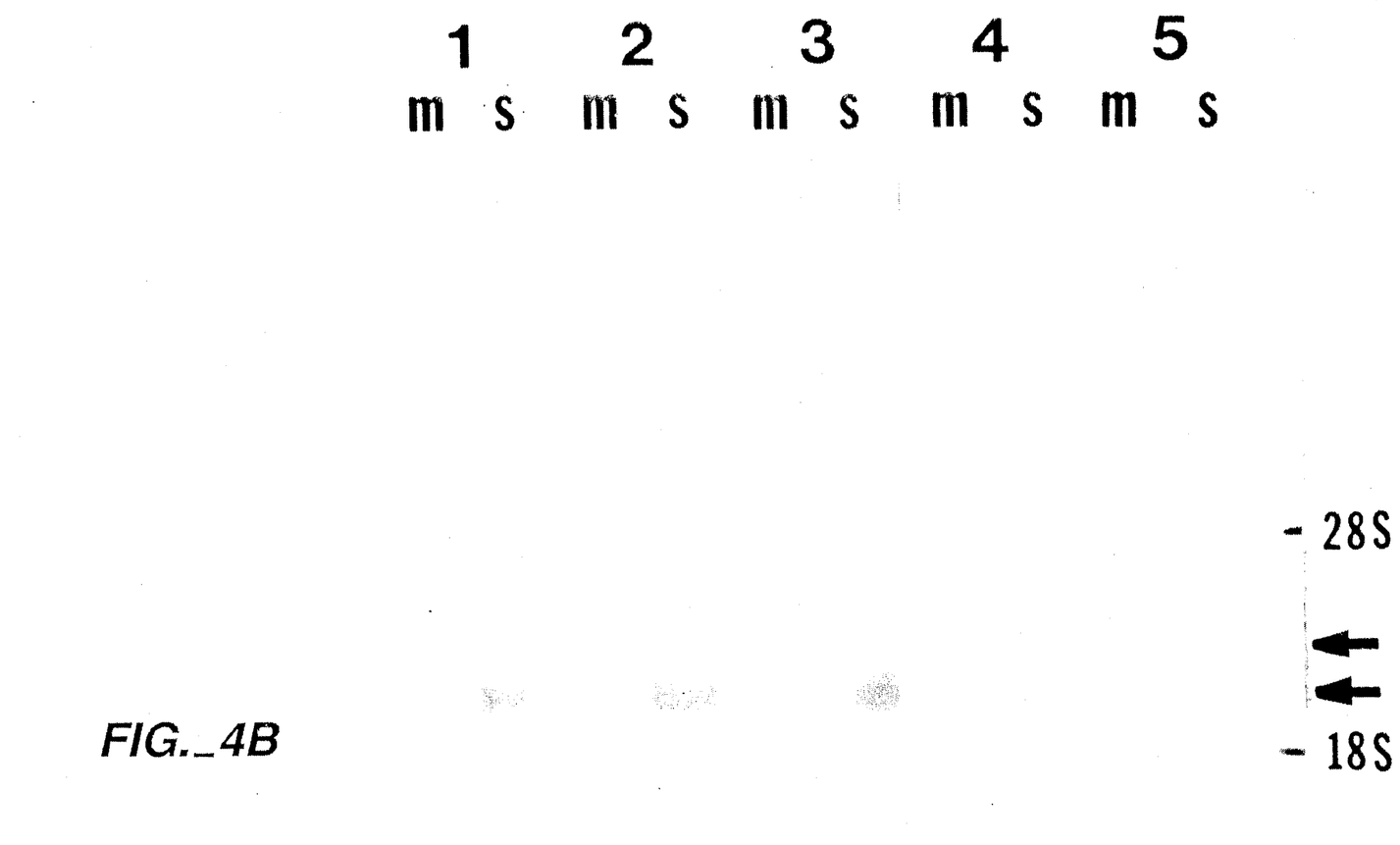

To determine whether HTLV-I anti-sense RNA accumulates in infected cells, poly(A)+RNA blots of SLBl (HTLV-I positive) and Molt4 (HTLV-I negative)

human T cell line RNAs were probed using single-stranded, radiolabelled RNA probes. One microgram of poly(A)+enriched RNA was loaded in a 1.4% agarose gel and processed for blot analysis. The blot was cut into strips having one lane of each RNA, Molt4(m) and SLBl(s). The strips (lanes 1-5) were hybridized overnight at 63° C. with a corresponding RNA probe (1-5) indicated in the top portion of the figure. The probes were constructed by subcloning the HTLV-I segments indicated in the figure from an SLBl cDNA plasmid into pGEM4 (Promega Biotech), and generating radiolabelled RNA in vitro using either SP6 or T7 RNA-polymerase as described by the manufacturers (Promega Biotech). The p40x expression plasmid pSVMTEXΔX was constructed by inserting the mouse metallothionine promoter 5' to an envelope/pX cDNA (provided by Dennis Slamon, UCLA) that was cloned into a pCD-derived cDNA cloning vector (H. Okayama and P. Berg, Mol. Cell Biol. 5, 1136(1985). The sequences between the two Xho I sites in the envelope gene were deleted. The frameshift mutated pX expression plasmid, pSVMTEXΔX resulting in a 2 base pair insertion at the 5' end of the p40x reading frame. As shown in FIG. 4, a 2.5 kb anti-sense RNA was detected in the SLBl cells, but not in the Molt4 cells, with 3 separate contiguous probes extending from base 5159 and 7020 of the HTLV-I genome (FIG. 4, lanes 1-3, lower arrow). Thus anti-sense transcription occurs through most of the anti-sense orf-IV (see FIG. 2) and continues through the complementary strand of the entire envelope coding sequence including orf-I (see FIG. 2). It is interesting to note that the 2.5Kb anti-sense message corresponds closely to the complement of the second intron of the p40x precursor RNA. This message begins at approximately nucleotide number 918 and ends at 3818 thus including sequences I, IV, and V from Table 1 above.

A larger and less abundant 2.9Kb RNA was detected with a probe to the complementary strand of the p40x coding region (FIG. 4, lane 4, upper arrow). If the 2.5Kb RNA initiates within the 1.8 Kb 3' terminus of the provirus as suggested by the CAT assay results (Example 2 and 3), it must either initiate very close to the junction of probes 3 and 4 or it is generated by splicing of a larger precursor since it is not detected with probe 4. The observed 2.9Kb RNA corresponds closely to what would be predicted for an unspliced transcript that initiated near the TATAAA (base 8145) and terminated near the AATAAA (base 5228) on the anti-sense strand of the provirus. We did not detect significant levels of discrete anti-sense RNAs with the 3' LTR probe (FIG. 3, lane 5) although a faint smear was observed near the 28s region. Low abundancy, higher molecular weight RNAs were also detected with probes 1-3. These might represent transcripts that continue into the gag and pol regions of the genome. Thus, anti-sense mRNA's derived from the HTLV-I virus can be detected in infected cells using probes 1-4. Probes to other regions of the anti-sense genome may detect other anti-sense mRNA's.

What we claim is:

1. A polypeptide which is expressed by the anti-sense strand of the HTLV-I viral genome and having one of the following sequences:

(I)

Arg-Arg-Met-His-Gly-Pro-Ala-Arg-Ile-Thr-Arg-Arg-Ser-Ser-Ala-Thr-Arg-Val-Ile-Pro-Val-Cys-Lys-Ala-Ser-Arg-Ala-His-Cys-Glu-Arg-Pro-Arg-Ser-Gln-Leu-Arg-Pro-Gln-Pro-Val-Arg-Thr-Arg-Phe-Ser-Arg-Gly-Gly-Leu-Ser-Cys-Ser-Ile-Gly-Thr-Trp-Glu-Leu-Val-Ile-Phe-Gly-Lys-Arg-His-Cys-Ser-Cys-Asn-Ala-Leu-His-Asn-Pro-Pro-Cys-Ser-Gln-Asn-Arg-Arg-Ser-Arg-Pro-Arg-Leu-Phe-Trp-Ala-Ala-Tyr-Cys-Ala-Ile-Leu-Ser-Arg-Phe-Leu-Trp-Phe-Leu-Thr-Ile-Ala;

(II)

Ser-Pro-Lys-Met-Arg-Gly-Gln-Asn-Trp-Lys-Asn-Lys-Ile-Lys-Val-Ala-Arg-Asn-Leu-Pro-Met-Val-Leu-Glu-Val-Phe-Phe-Phe-Gly-Ile-Gly-Gly-Ala-Ser-Asp-Gly-Ser-Trp-Ala-Cys-Ser-Ser-Leu-Glu-Glu-Ser-Pro-Arg-Asp-Pro-Leu-Gly-Arg-Thr-Ser-Ala-Tyr-Arg-Asp-Glu-Ser-Ser-Ala-Gly-Ser-Phe-Leu-Glu-Ser-Leu-Leu-Trp-Ser-Phe-Pro-Leu-Ala-Ala-Ile-Lys-Thr-Arg-Lys-Leu-Glu-Ile-Ile-Pro-Met-Gly-Leu-Phe-Ile-Ala-Glu-Gly-Thr-Cys-Leu-Trp-Asp-Arg-Leu-Glu-Ser-Gly-Gly-Val-Val-Lys-Leu-Pro-Ser-Gly-Phe-Val-Ala-Val-Gly;

(III)

Arg-Val-Ser-Gly-Pro-Gln-Val-Val-Asp-Glu-Ser-Pro-Gly-Ser-Ile-Gly-Leu-Phe-Asn-Trp-Glu-Tyr-Trp-Val-Ile-Pro-Trp-Pro-Gly-Val-Gly-Phe-Asp-Met-Ala-Cys-Leu-Gln-Gly-Leu-Pro-Asp-Gln-Val-Leu-Gln-Gly-Leu-Glu-Ala-Phe-Trp-Phe-Lys-Gly-Asn-Trp-Leu-Ile-Ser-Gly-Gly-Leu-Gly-Arg-Cys-Ser-Ser-Pro-Arg-Thr-Ala-Gly-Ala-Cys-Ile-Gly-Lys-Ile-Thr-Gly-Gly-Leu-Phe-Ala-Ser-Gly-Arg-Tyr-Arg-Thr-Pro-Trp-His-Cys-Cys-Lys-Ala-Ser-Arg-Pro-Met-Met-Ala;

(IV)

Ser-Asp-Ala-Leu-Asp-Arg-Trp-Pro-Val-Gly-Arg-Asp-Asp-Val-Gly-Gly-Pro-Asn-Ile-Val-Pro-Gln-Arg-Trp-Gly-Thr-Ser-Arg-Leu-Val-His-Ser-Leu-Gln-Thr-Arg-Arg-Leu-Gly-Ile-Arg-Lys-Glu-Asp-Ser-Val-Gln-Thr-Leu-Gly-Ser-Gly-Leu-Ile-Ile-Ser-Met-Val-Asn-Phe-Val-Ser-Ala-Gly-Leu-Phe-Arg-Cys-Leu-Pro-Val-Ser-Cys-Pro-Glu-Asp-Leu-Leu-Val-Glu-Glu-Leu-Val-Asp-Gly-Leu-Leu-Ser-Leu-Glu-Glu-Glu-Leu-Lys-Asp-Lys-Glu-Glu-Glu-Glu-Ala-Val-Leu-Asp-Gly-Leu-Leu-Ser-Leu-Glu-Glu-Glu-Ser-Arg-Gly-Arg-Leu-Arg-Arg-Gly-Pro-Pro-Gly-Glu-Lys-Ala-Pro-Pro-Arg-Gly-Glu-Thr-His-Arg-Asp-Arg-Gln-Arg-Arg-Ala-Glu-Glu-Lys-Arg-Lys-Arg-Lys-Lys-Glu-Arg-Glu-Lys-Glu-Glu-Glu-Lys-Gln-Thr-Ala-Glu-Tyr-Leu-Lys-Arg-Lys-Glu-Glu-Glu-Lys-Ala-Arg-Arg-Arg-Arg-Arg-Ala-Glu-Lys-Lys-Ala-Ala-Asp-Val-Ala-Arg-Arg-Lys-Gln-Glu-Glu-Gln-Glu-Arg-Arg-Glu-Arg-Lys-Trp-Arg-Gln-Gly-Ala-Glu-Lys-Ala-Lys-Gln-His-Ser-Ala-Arg-Lys-Glu-Lys-Met-Gln-Glu-Leu-Gly-Ile-Asp-Gly-Tyr-Thr-Arg-Gln-Leu-Glu-Gly-Glu-Val-Glu-Ser-Leu-Glu-Ala-Glu-Arg-Arg-Lys-Leu-Leu-Gln-Glu-Lys-Glu-Asp-Ser-Leu-Met-Gly-Glu-Val-Asn-Tyr-Trp-Gln-Gly-Arg-Leu-Glu-Ala-Met-Trp-Leu-Gln; and (V)

Gly-Pro-Cys-Gly-Glu-Gly-Asn-Phe-Ile-Glu-Glu-Phe-Phe-Tyr-Ser-Leu-Val-Gly-Asn-Ile-Gly-Glu-Glu-Gly-Pro-Glu-Leu-Ala-Gly-Val-Ala-Lys-Asn-His-Val-Gly-Gln-Glu-Gly-Pro-Gly-Asp-Gly-Gly-Gly-Lys-Leu-Val-Glu-Val-His-Ala-Asp-Asn-Gly-Ala-Ser-Pro-Glu-Gly-Val-Gln-Val-Leu-Gly-Pro-Glu-Ser-Gly-Val-Trp-Lys-Arg-Gln-Gly-Trp-Glu-Val-Leu-Pro-Lys-Gly-Gly-Phe-His-Val-Ser-Ile-Ser-Glu-Gly-Gly-Val-Phe-Ala-His-Gly-Leu-Glu-Glu-Gly-Gly-Trp-Asn-Val-Gly-Gly-Cys-Met-Ser-Asp-Trp-Arg-Gly-Lys-Asp-Leu-Glu-Gly-Leu-Arg-Gly-Ser-Leu-Gly-Gly-Glu-Gly-Gly-Glu-Ser-Arg-Asp-Lys-Glu-Leu.

* * * * *